United States Patent [19]

Phipps

[11] Patent Number: 5,260,073
[45] Date of Patent: Nov. 9, 1993

[54] USE OF PHENYLPROPANOLAMINE AS A MUCUS SECRETOGOGUE IN THE UPPER AIRWAYS

[75] Inventor: Roger J. Phipps, Sherburne, N.Y.

[73] Assignee: Norwich Eaton Pharmaceuticals, Inc., Norwich, N.Y.

[21] Appl. No.: 893,956

[22] Filed: Jun. 4, 1992

Related U.S. Application Data

[63] Continuation of Ser. No. 526,218, May 21, 1990, abandoned.

[51] Int. Cl.$^5$ .............. A61K 9/08; A61K 9/20; A61K 9/48
[52] U.S. Cl. .............. 424/465; 424/451; 424/457; 424/464; 424/468; 514/849; 514/853
[58] Field of Search .............. 424/464, 465, 451, 441, 424/400; 514/853

[56] References Cited

U.S. PATENT DOCUMENTS

| | | | |
|---|---|---|---|
| 4,083,950 | 4/1978 | Duvall et al. | 424/44 |
| 4,619,934 | 10/1986 | Sunshine et al. | 514/277 |
| 4,738,966 | 4/1988 | Sunshine et al. | 514/277 |
| 4,749,697 | 6/1988 | Sunshine et al. | 514/226.5 |
| 4,749,711 | 6/1988 | Sunshine et al. | 514/226.5 |
| 4,749,720 | 6/1988 | Sunshine et al. | 514/532 |
| 4,749,721 | 6/1988 | Sunshine et al. | 514/532 |
| 4,749,722 | 6/1988 | Sunshine et al. | 514/567 |
| 4,749,723 | 6/1988 | Sunshine et al. | 514/567 |
| 4,818,541 | 4/1989 | Sanderson | 424/448 |
| 4,839,354 | 6/1989 | Sunshine et al. | 514/226.5 |
| 4,840,962 | 6/1989 | Sunshine et al. | 514/406 |
| 4,894,233 | 1/1990 | Sharma | 424/465 |

OTHER PUBLICATIONS

Gallagher, J. T. et al., "The composition of tracheal mucus and the nervous control of its secretion in the cat," 192 Proc. R. Soc. Long. B., 49–76 (1975).
Wells, U. et al., "Lateral Nasal Gland Secretion in the Anaesthetized Dog," 374 J. Physiol., 359–374 (1986).
Phipps, R. J. et al., "Effect of Alpha-Adrenergic Stimulation on Mucus Secretion and on Ion Transport in Cat Trachea In Vitro$^{1-3}$," 121 American Review of Repiratory Disease, 359–365 (1980).
Phipps, R. J. et al., "Sympathomimetic drugs stimulate the output of secretory glycoproteins from human bronchi in vitro," 63 Clinical Science, 23–28 (1982).
WPI66-07742F/00, date Mar. 1962, France (Eng. Abs*).
WPI84-152447/25, date Feb. 1984, Belgium (Eng. Abs*).
WPI66-00688F/00, date Jan. 1968, Great Britain (Abs*).
WPI20269 K/09, date Jun. 1981, Germany (Eng. Abs*).
WPI66-19205F/00, date Jun. 1959, Japan (Eng. Abs*).
L. Lasagna, Phenylpropanolamine: A review. (1988) (pp. 7–12; 24–25; 28–29; 138; 302; 317; 320–345).
M. Bende and L. Laurin, "Sympathomimetrics in Nasal Allergy," J. Otorhinolaryngol. Relat. Spec. 48(4):238–242), 1986.
S. Loth and M. Bende, "The Effect of Phenylpropanolamine on Nasal Secretion and Nasal Airway Resistance After Histamine Challenge in Man." Clin. Otolaryngol. 10(1):15–19 (Feb.) 1985.
Drug Facts and Comparisons, 1990 ed. Copyright 1989 published by J. B. Lippincott Co., St. Louis, Mo.

Primary Examiner—Thurman K. Page
Assistant Examiner—Amy Hulina
Attorney, Agent, or Firm—Joanne P. Will; Karen F. Clark; David L. Suter

[57] ABSTRACT

The present invention encompasses the novel method of using ±phenylpropanolamine to induce mucous secretion in the upper airways of persons afflicted with sinusitis or otitis media characterized by retention of thickened respiratory secretions. These methods comprise administering to such person a safe and effective amount of ±phenylpropanolamine. It also encompasses certain novel oral compositions consisting essentially of l(−)-norephedrine and a pharmaceutically-acceptable excipient base.

5 Claims, No Drawings

USE OF PHENYLPROPANOLAMINE AS A MUCUS SECRETOGOGUE IN THE UPPER AIRWAYS

This is a continuation of application Ser. No. 526,218, filed on May 21, 1990, now abandoned.

BACKGROUND OF THE INVENTION

This invention relates to (1) the novel method of using ±phenylpropanolamine to induce mucous secretion in the upper airways of persons afflicted with sinusitis or otitis media characterized by retention of thickened mucus and respiratory secretions and (2) certain novel compositions of l(−)-norephedrine and a pharmaceutically acceptable excipient base.

Phenylpropanolamine is a sympathomimetic compound administered orally as an anorectic and as a nasal decongestant. The compound has two chiral centers as shown in the following structural formula (the two chiral carbons, labeled alpha and beta, are denoted by an asterisk):

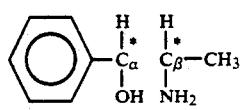

This results in four optical isomers, listed as follows with their common names and absolute configurations:

| Isomer | Alpha | Beta |
| --- | --- | --- |
| d(+)-norephedrine | S | R |
| l(−)-norephedrine | R | S |
| d(+)-norpseudoephedrine | S | S |
| l(−)-norpseudoephedrine | R | R |

A substance that rotates plane-polarized light in a clockwise direction is said to be dextrorotatory and the rotation is said to be positive. A substance that rotates plane polarized light in a counterclockwise direction is said to be levorotatory and the rotation is said to be negative (Solomons, *Organic Chemistry*, p. 246 (1978)).

The most active isomers physiologically for known uses are those with the S-configuration on the beta carbon atom (Lasagna, *Phenylpropanolamine—A Review*, p.28 (1980)). These are l (−)-norephedrine d(+)-norpseudoephedrine. The d(+)-norpseudoephedrine isomer is a naturally occurring substance found primarily in the shrub *Catha edulis* and is used orally in Europe for its anorectic properties at a dose of about 40–50 mg/day. A racemic mixture of d(+)-norephedrine and l(−)-norephedrine, generally referred to as either +phenylpropanolamine or phenylpropanolamine, is marketed as an anorectic at a dose of about 50–75 mg/day, and as a nasal decongestant at a dose of about 75–150 mg/day.

The four isomers of phenylpropanolamine are described in the literature. However, these four isomers have never been suggested to have nasal mucosecretory effects. For example, U.S. Pat. No. 4,818,541 issued to Sanderson on Apr. 4, 1989, discloses a method of inducing anorexia or nasal decongestion by the transdermal administration of any of the four isomers of phenylpropanolamine.

Persons afflicted with sinusitis or otitis media may suffer from nasal congestion, eustachian tube congestion and retention of respiratory mucus. Many persons who suffer from sinusitis or otitis media have both upper respiratory congestion and retention of thickened respiratory secretions. Antimicrobials are used to treat the infection in sinusitis and otitis media while decongestants are used to treat the congestion. Medications that promote upper respiratory decongestion constrict blood vessels in the upper respiratory tract; this reduces the tissue volume and thus provides decongestion of congested tissues, such as tissues in the nose, eustachian tubes and sinuses.

The prior art teaches that the constriction of nasal blood vessels reduces fluid in nasal tissues. The fluid in these tissues has two sources: (1) transudation which is the loss of fluid from the nasal blood vessels into the nasal tissues and (2) active secretion from cells in the respiratory mucosa and the nasal glands that secrete mucus. In healthy persons, there is little transudation. But transudation is increased greatly during infection and inflammation when the blood vessels become more permeable. Decongestants reduce transudation by constricting nasal blood vessels.

Decongestants have not been considered to provide complete relief from nasal congestion and retention of a particular thickened respiratory secretion, thickened mucus, since they are not known to promote mucous secretion and elimination of the retained mucus. Enhanced active secretion of mucus from cells in the respiratory mucosa and the nasal glands that secrete mucus would be beneficial to a person with thickened retained secretions and/or infection. Increased mucous secretions would help liquefy any thickened retained secretions (especially in the sinuses) and hence facilitate their drainage. Increased mucous secretions would also increase the flux of antimicrobial molecules onto the mucosa to combat the cause of the infection. In particular, mucous secretions increase the flux of antibacterial molecules in the mucus that combat the cause of the infection and they help liquefy any thickened, retained secretions (especially in the sinuses) and hence facilitate their drainage.

SUMMARY OF THE INVENTION

It has been discovered that both l(−)-norephedrine and d(+)-norephedrine, alone or in combination, are active as mucosecretory agents. However, l(−)-norephedrine is a more potent mucus secretogogue than d(+)-norephedrine.

The present invention encompasses the novel method of using phenylpropanolamine (defined herein as d(+)-norephedrine or l(−)-norephedrine or mixtures of d(+)-norephedrine and l(−)-norephedrine; henceforth referred to as "PPA") to induce mucous secretion in the upper airways of persons afflicted with sinusitis or otitis media characterized by retention of thickened respiratory secretions. These methods comprise orally administering to such person a safe and effective amount of PPA. It also encompasses certain novel oral compositions consisting essentially of l(−)-norephedrine and a pharmaceutically-acceptable excipient base.

DESCRIPTION OF THE INVENTION

The present invention encompasses certain novel methods and compositions useful for inducing mucous secretion in the upper airways of a person afflicted with sinusitis or otitis media characterized by retention of thickened respiratory secretions. Specific compounds and compositions to be used in the invention must, accordingly, be pharmaceutically-acceptable. As used herein, such a "pharmaceutically-acceptable" component is one that is suitable for use with humans without undue adverse side effects (such as toxicity, irritation and allergic response) commensurate with a reasonable benefit/risk ratio.

METHOD OF TREATMENT

The present invention encompasses a method of inducing mucous secretion in the upper airways of a human afflicted with sinusitis or otitis media characterized by retention of thickened respiratory secretions, comprising systemically administering to said subject a safe and effective amount of a compound selected from the group consisting of d(+)-norephedrine, l(−)-norephedrine and mixtures thereof.

Sinusitis is an inflammation of the mucous membranes of the paranasal sinuses. It can result from inflammation caused by bacteria, allergy, viruses, or a closing of the sinus ostium as a result of any cause (e.g. change in pressure or physical obstruction). Sinusitis is usually classified as: (1) acute, congestive—this is the initial stage of inflammation/infection; (2) acute, purulent—the progression of bacterial infection from untreated/unresolved acute congestive form; (3) chronic, purulent —untreated, unresolved acute sinusitis with permanent tissue destruction and tissue changes. The definition of sinusitis is more fully described in Ballenger, *Diseases of the Nose, Throat, Ear, Held and Neck*, p. 207 (1985) and Geldman, *The Principles and Practice of Rhinology*, p. 89 (1987), which are incorporated by reference herein.

Otitis media is an inflammation of the mucous membranes of the middle ear cavity. As with sinusitis, it can result from bacteria, allergy, viruses, or a blockage of the eustachian tube from other causes (e.g. pressure changes or physical obstructions). Acute otitis media is the acute stage of infection (usually bacterial infection), with fluid or pus (purulent secretions) in the middle ear. Serous or secretory otitis media occurs when there is fluid in the middle ear cavity with no associated infection (i.e. the fluid is sterile). This can occur as a result of a non-infectious cause of eustachian tube closure, or from treated acute otitis media wherein fluid is retained in the middle ear. Chronic otitis media is the untreated/unresolved acute condition, with permanent tissue destruction and tissue changes. Otitis media is further described in Ballenger, *Diseases of the Nose, Throat, Ear, Head and Neck*, pp. 1113–1140 (1985), which is incorporated by reference herein.

The term "nasal congestion" refers to an increase in resistance to nasal air flow caused by increased blood volume in the nasal tissues. The term "upper respiratory" or "upper airways" refers to the eustachian tube and middle ear and the region of the respiratory tract above the larynx. This includes the pharynx, nasopharynx, nasal cavity (vestibule, septum, turbinates, olefactory region) and paranasal sinuses (sphenoid, ethmoid, maxillary and frontal). "Respiratory secretions" refers to any fluid covering the mucosa of the "upper respiratory" tract. In the nasal airways these respiratory secretions result mainly from active secretion of the components from specific secretory structures. These secretions also consist of protein and other substances "leaking" from the blood vessels onto the mucosa during inflammation of the mucosa (e.g. sinusitis, otitis media and rhinitis). A type of thickened respiratory secretion is "thickened mucus" which is mucus with abnormal physical properties (increased viscosity and/or elasticity). Quantitatively, thickened mucus has measurements within the range of 10–500 poise for apparent viscosity and 1–100 dynes/cm$^2$ for elastic modulus when measured at a shear rate of 0.3/sec.

The preferred techniques for measuring mucous viscoelasticity are capillary viscometry and magnetic micrometry. For capillary viscometry, a small sample of mucus (perhaps as little as 5 microliters) is drawn into a capillary tube of known dimensions. Pressure (or suction) applied to the tube causes the mucus to flow along the tube. Flow rate at constant pressure, and degree of recoil when pressure is removed, are indices of mucous viscosity and elasticity, respectively. For magnetic micrometry, a small (100–200 micrometers) iron sphere is placed into a mucus sample within a special chamber. This sphere is oscillated at known frequency by sinusoidal magnetic forces; the amplitude of oscillation is an index of both elastic modulus (elasticity) and loss modulus (viscosity). Capillary viscometry and magnetic microrheometry are further described in: Philippoff (W.), Han (C.D.), Barnett (B.), Dulfano (M.J.), "A Method for Determining the Viscoelastic Properties of Biological Fluids", *Biorheology*, pp. 55–67 (1970); Lutz (R.J.), Litt (M.), Chakrin (L.), "Physical-Chemical Factors in Mucus Rheology", *Rheology of Biological Systems*, H. L. Gabelnick and M. Litt (eds.), Thomas, Springfield, pp. 119–157 (1973), which are incorporated herein by reference.

These abnormal physical properties can result from enhanced secretion of proteins/glycoproteins relative to water, from inflammation (influx of inflammatory cells, such as monocutes and neutrophils, from the blood and tissues), from tissue damage causing release of substances (for example, fibrin and DNA) that cause mucous thickening, or from mucous dehydration by the reabsorption of water (or through any combination of these causes).

Typically, in this invention the dosage regimen consists of administration of PPA one to four times per day. Preferably, the PPA will be administered two to four times per day. Treatment regimens will extend for the duration of the sinusitis or otitis media. The PPA is preferably administered orally. For humans (assuming an approximate body weight of 70 kg) individual doses of from about 10 mg to about 100 mg of PPA are acceptable. Individual doses of from about 10 mg to about 50 mg are preferred.

A "safe and effective amount" of PPA is an amount that is effective to induce mucous secretion in a human afflicted with sinusitis or otitis media characterized by retention of thickened mucus and respiratory secretions, without undue adverse side effects (such as toxicity, irritation, or allergic response) commensurate with a reasonable benefit/risk ratio when used in the manner of this invention. This specific "safe and effective amount" will, obviously, vary with such factors as the duration of treatment, the nature of concurrent therapy (if any), the specific dosage form to be used, the carrier employed, and the dosage regimen desired for the composition. As used herein, the phrase "to induce mucous secretion" means to either (a) produce an increase in the amount of mucus secreted by a person who is presently secreting mucus or (b) to cause mucus to be secreted by a person who is not presently secreting mucus.

COMPOSITIONS

The present invention also provides oral compositions for inducing upper respiratory mucous secretion consisting essentially of (a) a safe and effective amount of l(−)-norephedrine; and (b) a pharmaceutically-acceptable excipient base.

These compositions can additionally contain a second optional compound selected from the following classes of compounds: non-narcotic analgesic non-steroidal drugs, non-narcotic analgesic non-steroidal anti-inflammatory drugs, antibacterials, antihistamines, antitussives or expectorants and combinations thereof.

Non-narcotic analgesic non-steroidal drugs among those useful include, but are not limited to, acetaminophen.

Non-narcotic analgesic non-steroidal anti-inflammatory drugs among those useful include, but are not limited to, the following: aspirin, phenacifin, indomethacin, sulindac, zomepirac, tolmefin sodium, mefenamic acid, meclofenamate sodium, diflunisal, flufenisal, piroxican, sudoxican, isoxican, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, and pharmaceutically acceptable salts thereof. Preferred non-narcotic analgesic non-steroidal anti-inflammatory drugs are aspirin, ibuprofen and naproxen.

Antibacterials among those useful include, but are not limited to, the following: cefaclor, cefadroxil, cefuroxime axetil, cephalexin, cephradine, cefixime, cefcanel daloxate, cefteram pivoxil, cefpodoxime, ampicillin, amoxicillin, bacampicillin, carbenicillin, cloxacillin, dicloxacillin, oxacillin, penicillin, nafcillin, lorcarbocef, amoxicillin+clavulanic acid, nalidixic acid, cinoxacin, oxolinic acid, pipemedic acid, pefloxacin, ciprofloxacin, enoxacin, temafloxacin, tosufloxacin, amifloxacin, lomefloxacin, ofloxacin, fleroxacin, irloxacin, rufloxacin, erythromycin, sulfamethizole, sulfamethoxazole, sulfisoxazole, tetracycline, oxytetracycline, doxycycline, trimethoprim, trimethoprim/sulfamethoxazole. Preferred antibacterials include: cefaclor, amoxicillin, amoxicillin+clavulanic acid, cefixime, ciprofloxacin, trimethoprim/sulfamethoxazole.

Antihistamines among those useful include, but are not limited to, the following: chlorpheniramine, brompheniramine, dexchlorpheniramine, dexbrompheniramine, tripolidine, diphenhydramine, doxylamine, tripelennamine, cyproheptadine, carbinoxamine, bromodiphenhydramine, phenindamine, pyrilamine, azatadine, terfenadine, astemizole, loratadine, acrivastine, cetirizine, azalastine, evastine, levocabastine, and pharmaceutically acceptable salts thereof. Preferred antihistamines include: chlorpheniramine, diphenhydramine, phenindamine, pyrilamine, terfenadine, astemizole, loratadine, acrivastine, cetirizine and azalastine.

Antitussives among those useful include, but are not limited to, the following: dextromethorphan, codeine, terpin hydrate and pharmaceutically acceptable salts thereof. Preferred antitussives include: dextromethorphan and codeine.

As used herein, "expectorant" does not refer to l(−)-norephedrine, d(+)-norephedrine, l(−)-norpseudoephedrine or d(+)-norpseudoephedrine. Expectorants among those useful include, but are not limited to, the following: guaifenesin, potassium guaicolsulfonate, potassium iodide, potassium citrate, iodinated glycerol, acetylcysteine, carboxymethylcysteine, ambroxol, sobrerol, and pharmaceutically acceptable salts thereof. Preferred expectorants include: guaifenesin, carboxymethylcysteine, iodinated glycerol, acetylcysteine, ambroxol and sobrerol.

The compositions of this invention are preferably provided in unit dosage form. As used herein, a "unit dosage form" is a composition of this invention containing an amount of l(−)-norephedrine that is suitable for administration to a human, in a single dose, according to good medical practice.

The racemic mixtures of dl-norephedrine or dl-norpseudoephedrine (in the form of either the free bases or the hydrochloride salts) may be separated from each other by fractional crystallization, taking advantage of their different solubilities.

The following melting points (mp) were reported for the purified racemates (Hoover, F. W., & Hass, H. B., Synthesis of 2-amino-1-phenyl-1-propanol and Its Methylated Derivatives, *J. Org. Chem.*, Vol. 12, pp. 506–509 (1947)).

|  | dl-Norephedrine |  | dl-Norpseudoephedrine |
|---|---|---|---|
| Free base | mp 104°–105° | | mp 71° C. |
| HCL salt | mp 192° C. | | mp 169° C. |

Each racemic mixture can be resolved into the corresponding enantiomers by conversion of the amines to salts of optically pure tartaric acid (Kalm, M. J., "3-imidomethyloxazolidines," *J. Org. Chem.*, Vol. 25, pp. 1929–1937 (1960)). These salts are diastereoisomers that can be separated by fractional crystallization, and the amines can then be regenerated by treatment with alkali. The scheme shown in the figure below summarizes the method of resolution, using the dl-norephedrine racemate as an example. The separation of the racemic mixtures of dl-norephedrine or dl-norpseudoephedrine is more fully described in Lasagna, *Phenylpropanolamine-A Review*, p. 30, (1980), incorporated herein by reference.

The following schematic describes the resolution of dl-norephedrine into corresponding enantiomers.

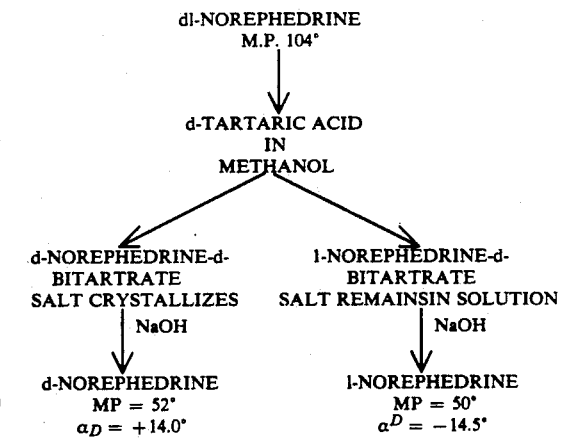

The unit dosage from will typically contain from 10 mg to 100 mg of l(−)-norephedrine. Preferably, the unit dosage form will be from 10 mg to 50 mg of l(−)-norephedrine.

The compositions of this invention may be in any of a variety of forms. Many different pharmaceutically-acceptable excipient bases well-known in the art may be used. These include, but are not limited to, solid or liquid fillers, diluents, co-solvents, surfactants, and encapsulating substances. The amount of excipient base employed in conjunction with l(−)norephedrine is sufficient to provide a practical quantity of material for administration per unit dose of the l(−)-norephedrine. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2nd Edition (1976).

The l(−)-norephedrine may be administered as an immediate release dosage form such as a liquid, a capsule or a tablet using an excipient base or it may be incorporated into a polymer excipient base to provide a long acting dosage form. Preferably, the excipient base or polymer excipient base comprises at least 50% by weight of the dose form.

A preferred immediate release liquid comprises:
(a) l(−)norephedrine at a level from about 0.5 to 5.0%; and
(b) an optional active ingredient selected from the group consisting of non-narcotic analgesic non-steroidal anti-inflammatory drugs, non-narcotic analgesic non-steroidal drugs, antibacterials, analgesics, expectorants, antihistamines, antitussives, and combinations thereof at a level from 0% to 50%; and
(c) a solvent at a level from about 50% to 95%; and
(d) a co-solvent at a level from about 5% to 20%; and
(e) a buffer system at a level from about 0.05% to 5%; and
(f) a surfactant at a level from about 0.1% to 5%; and
(g) a preservative at a level from about 0.004% to 1%; and
(h) a sweetening agent at a level from about 0.25% to 20%; and
(i) a flavoring agent at a level from about 0.01% to 2%; and
(j) pharmaceutical grade dyes or pigments may be used at levels from about 0.05% -2.0%; and
(k) a viscosity modifier at a level from about 2% to about 15% (all percentages are by weight of the composition).

A preferred solvent is water.

Flavoring agents among those useful herein are described in the following reference, incorporated by reference herein: *Remington's Pharmaceutical Sciences*, 16th Edition, Mack Publishing Company, 1980, pp. 1230-1239. Dyes or pigments among those useful herein are described in the following reference, incorporated by reference herein: *Handbook of Pharmaceutical Excipients*, pp. 81-90, 1986 by the American Pharmaceutical Association & the Pharmaceutical Society of Great Britain.

Preferred co-solvents are ethanol, sorbitol, glycerin, propylene glycol, polyethylene glycol.

Preferred buffer systems include boric, carbonic, phosphoric, succinic, malic, tartaric, citric, acetic, benzoic, lactic, glyceric, gluconic, glutaric and glutamic. Particularly preferred are phosophoric, tartaric and citric.

Preferred surfactants include polyoxyethylene sorbitan fatty acid esters, polyoxyethylene monoalkyl ethers, sucrose monoesters and lanolin esters and ethers.

Preferred preservatives are phenol, alkyl esters of parahydroxybenzoic acid, o-phenyl phenol benzoic acid and its salts, boric acid and its salts, sorbic acid and its salts, chlorbutanol, benzyl alcohol, thimerosal, phenylmercuric acetate and nitrate, nitromersol benzalkonium chloride, cetylpyridinium chloride, methyl paraben, and propyl paraben. Particularly preferred are salts of benzoic acid, cetylpyridinium chloride, methyl paraben and propyl paraben.

Preferred sweeteners include sucrose, glucose, saccharin, aspartame. Particularly preferred are sucrose and saccharin.

Preferred viscosity agents include methylcellulose, sodium carboxymethylcellulose, hydroxypropylmethylcellulose, carbomer, povidone, acacia, guar gum, xanthine gum and tragacanth. Particularly preferred are methylcellulose, xanthine gum, guar gum, povidone and sodium carboxymethylcellulose.

A preferred immediate release capsule comprises:
(a) l(−)-norephedrine at a level from about 2% to about 30%; and
(b) an optional active ingredient selected from the group consisting of non-narcotic analgesic non-steroidal anti-inflammatory drugs, non-narcotic analgesic non-steroidal drugs, antibacterials, analgesics, expectorants, antihistamines, antitussives, and combinations thereof at a level from 0% to 50%; and
(c) a filler at a level from about 20% to about 70%; and
(d) a disintegrant at a level from about 0.1% to about 3%; and
(e) a lubricant at a level from about 0.5% to about 6%.

An immediate release tablet is preferably formulated in an excipient base that contains one or more of the components listed above for capsule formulation plus the following components:
(f) a binder at a level from about 1.0% to about 10%; and
(g) pharmaceutical grade dyes or pigments may be used at levels from about 0.05%-2.0% (all percentages are by weight of the dose form).

Dyes or pigments among those useful herein are described in the following reference, incorporated by reference herein: *Handbook of Pharmaceutical Excipients*, pp. 81-90, 1986 by the American Pharmaceutical Association & the Pharmaceutical Society of Great Britain.

Preferred fillers include calcium sulfate, compressible sugar, dibasic calcium phosphate, starch, microcrystalline cellulose, lactose, sucrose and mannitol. Particularly preferred are lactose, microcrystalline cellulose and compressible sugar.

Preferred disintegrants include sodium starch glycolate, croscarmellose sodium, crospovidone, starch, microcrystalline cellulose, alginic acid, soy polysaccharides, and sodium carboxymethylcellulose. Particularly preferred are sodium starch glycolate, crospovidone and croscarmellose sodium.

Preferred binders include methylcellulose, sodium carboxymethylcellulose, hydroxypropylmethylcellulose, ethyl cellulose, acacia, gelatin, sucrose, polyvinylpyrrolidone, and guar gum. Particularly preferred are polyvinylpyrrolidone, methylcellulose and hydroxypropylmethylcellulose.

Preferred lubricants include magnesium stearate, zinc stearate, calcium stearate, stearic acid, hydrogenated vegetable oils, glycerol palmitostearate, sodium lauryl sulfate, polyethylene glycol, and talc. Particularly preferred are magnesium stearate, zinc stearate and sodium lauryl sulfate.

A preferred long acting dosage form comprises:
(a) l(−)-norephedrine at a level from about 2% to about 20%.
(b) an optional active ingredient selected from the group consisting of non-narcotic analgesic non-steroidal anti-inflammatory drugs, non-narcotic analgesic non-steroidal drugs, anti bacterials, expectorants, antihistamines, antitussives, and combinations thereof at a level from 0% to 20%; and
(c) a polymer material at a level of from about 10% to about 40%; and
(d) a lubricant at a level of from about 0.1% to about 6%; and
(e) a filler at a level of from about 20% to about 70%; and
(f) pharmaceutical grade dyes or pigments may be used at levels from about 0.05% to about 2% (all percentages are by weight of the dose form).

Preferably, the polymer material is selected from the group consisting of: cellulose ethers (such as methylcellulose, hydroxypropylmethylcellulose, hydroxypropylcellulose, and sodium carboxymethylcellulose), polyvinylpyrrolidone, mixtures of natural hydrophilic gums (such as guar gum, gum Karaya, gum tragacanth, and xanthine gum) synthetic hydrophilic polymers (such as carbomer) and mixtures thereof. Preferred are hydroxypropylmethylcellulose and mixtures of two or more cellulose ethers selected from the group consisting of methylcellulose, hydroxypropylcellulose, hydroxypropylmethylcellulose, and sodium carboxymethylcellulose and mixtures thereof. Particularly preferred are hydroxypropylmethylcellulose and carbomer.

The lubricants, fillers, dyes and pigments are identical to those described for the immediate release dose form.

The following non-limiting examples illustrate the compositions and uses of the present invention.

EXAMPLE I

An immediate release tablet composition, according to the present invention, is made comprising the following components:

| Ingredient | Per Tablet | Percent by Weight |
|---|---|---|
| l(−)-norephedrine hydrochloride | 37.5 mg | 22.0 |
| Terfenadine | 30.0 mg | 17.6 |
| Lactose | 65.0 mg | 38.1 |
| Hydroxypropylmethylcellulose | 15.0 mg | 8.8 |
| Croscarmellose sodium | 5.0 mg | 2.9 |
| Talc | 10.0 mg | 5.9 |
| Hydrogenated castor oil | 8.0 mg | 4.7 |
| | 170.5 mg | |

The tablet is made by wet granulating the l(−)-norephedrine hydrochloride, terfenadine and the lactose with a solution of hydroxypropylmethylcellulose. The granulation is dried, sized and the remaining ingredients are sequentially dry blended and then compressed into tablets.

EXAMPLE II

An immediate release tablet composition, according to the present invention, is made comprising the following components:

| Ingredient | Per Tablet | Percent by Weight |
|---|---|---|
| l(−)-norephedrine hydrochloride | 37.5 mg | 8.9 |
| Ibuprofen | 200.0 mg | 47.3 |
| Chlorpheniramine maleate | 8.0 mg | 1.9 |
| Dextromethorphan hydrobromide | 30.0 mg | 7.1 |
| Gelatin | 7.0 mg | 1.7 |
| Microcrystalline cellulose | 100.0 mg | 23.7 |
| Stearic acid | 15.0 mg | 3.5 |
| Polyethylene glycol | 15.0 mg | 3.5 |
| Calcium stearate | 10.0 mg | 2.4 |
| | 422.5 mg | |

The tablet is made by wet granulating the l(−)-norephedrine hydrochloride, ibuprofen, chlorpheniramine maleate, dextromethorphan hydrobromide with a gelatin solution. The granulatin is dried, sized and the remaining ingredients are sequentially dry blended and then compressed into tablets on a tablet press.

EXAMPLE III

An immediate release capsule composition, according to the present invention, is made comprising the following components:

| Ingredient | Per Capsule | Percent by Weight |
|---|---|---|
| l(−)-norephedrine | 25 mg | 19.5 |
| Lactose | 75 mg | 58.6 |
| Microcrystalline cellulose | 25 mg | 19.5 |
| Magnesium stearate | 2 mg | 1.6 |
| FD & C Yellow #6 Lake Dye | 1 mg | 0.8 |
| | 128 mg | |

The ingredients are sieved, sequentially dry blended and encapsulated on an automatic capsule filler.

EXAMPLE IV

An immediate release tablet composition, according to the present invention, is made comprising the following components:

| Ingredient | Per Tablet | Percent by Weight |
|---|---|---|
| l(−)-norephedrine | 30 mg | 15.8 |
| Dibasic calcium phosphate | 125 mg | 65.8 |
| Crospovidone | 5 mg | 2.6 |
| Microcrystalline cellulose | 25 mg | 13.2 |
| Zinc stearate | 5 mg | 2.6 |
| | 190 mg | |

The ingredients are sieved, sequentially dry blended and compressed into tablets on a tablet press.

EXAMPLE V

An immediate release chewable tablet composition, according to the present invention, is made comprising the following components:

| Ingredient | Per Tablet | Percent by Weight |
|---|---|---|
| l(−)-norephedrine | 37.5 mg | 5.7 |
| Sucrose (granular) | 300.0 mg | 45.3 |
| Mannitol (granular) | 300.0 mg | 45.3 |
| Sodium carboxymethylcellulose | 10.0 mg | 1.5 |
| Sodium lauryl sulfate | 6.0 mg | 0.9 |
| Stearic acid | 9.0 mg | 1.3 |
| | 662.5 mg | |

The ingredients are sieved, sequentially dry blended and compressed into tablets on a tablet press.

EXAMPLE XII

A thirty-five-year-old woman afflicted with sinusitis that is characterized by upper respiratory congestion and retention of thickened mucus and other thickened respiratory secretions is given a tablet formulated as in Example X four times a day. Administration of the above tablet results in decongestion and the drainage of mucus and respiratory secretions.

EXAMPLE XIII

A twenty-five-year-old man afflicted with sinusitis that is characterized by retention of thickened mucus and other thickened respiratory secretions is given a tablet formulated as in Example X four times a day. Administration of the above tablet results in the drainage of mucus and other respiratory secretions.

EXAMPLE XIV

A ten-year-old child afflicted with otitis media that is characterized by eustachian tube congestion and retention of thickened respiratory secretions, especially thickened mucus, is given a capsule formulated as in Example III four times a day. Administration of the above capsule results in the drainage of the mucus and other respiratory secretions.

EXAMPLE XV

A forty-three-year-old man afflicted with sinusitis characterized by retention of thickened respiratory secretions, especially thickened mucus, is given a tablet formulated as in Example V three times a day. Administration of the above tablet results in the drainage of mucus and other respiratory secretions.

EXAMPLE XVI

A thirty-seven year old man suffering from a persistent cough, postnasal drip and retention of thickened nasal and sinus mucus and other respiratory secretions is orally given a tablet formulated as in Example VI two times a day. Administration of the above tablet results in suppression of the persistent cough and drainage of the retained mucus and other respiratory secretions.

EXAMPLE VI

A long acting dosage composition, according to the present invention, is made comprising the following components:

| Ingredient | Per Unit Dose | Percent by Weight |
|---|---|---|
| l(−)-norephedrine | 50.0 mg | 11.6 |
| Compressible sugar | 250.0 mg | 57.8 |
| Carbomer | 100.0 mg | 23.1 |
| Stearic acid | 20.0 mg | 4.6 |
| Zinc stearate | 6.0 mg | 1.4 |
| FD & C Blue #2 Lake Dye | 6.5 mg | 1.5 |
| | 432.5 mg | |

The l(−)-norephedrine, compressible sugar, carbomer, stearic acid, and FD&C Yellow #6 Lake Dye are roller compacted, sized and the zinc stearate is then dry blended and tablets are then compressed on a tablet press.

EXAMPLE VII

A long acting dosage composition, according to the present invention, is made comprising the following components:

| Ingredient | Per Unit Dose | Percent by Weight |
|---|---|---|
| l(−)-norephedrine | 50 mg | 10.5 |
| Hydroxypropylmethylcellulose | 175 mg | 36.8 |
| Lactose | 225 mg | 47.4 |
| Talc | 15 mg | 3.2 |
| Magnesium stearate | 10 mg | 2.1 |
| | 475 mg | |

The l(−)-norephedrine and lactose are wet granulated with one third of the hydroxypropylmethylcellulose, dried and then sized. The remaining ingredients are sequentially dry blended and compressed on a tablet press.

EXAMPLE VIII

A long acting dosage composition, according to the present invention, is made comprising the following components:

| Ingredient | Per Unit Dose | Percent by Weight |
|---|---|---|
| l(−)-norephedrine | 40 mg | 7.3 |
| Hydroxypropylcellulose | 150 mg | 27.1 |
| Sucrose | 225 mg | 40.7 |
| Dibasic calcium phosphate | 100 mg | 18.1 |
| Sodium lauryl sulfate | 15 mg | 2.7 |
| Hydrogenated castor oil | 15 mg | 2.7 |
| FD & C Blue #2 Dye | 8 mg | 1.4 |
| | 553 mg | |

All the ingredients are sized, sequentially dry blended and compressed into tablets on a tablet press.

EXAMPLE IX

An immediate release liquid dosage composition, according to the present invention, is made comprising the following components:

| Ingredient | Per Liter | Percent (wt./volume) |
|---|---|---|
| Purified Water | 400.0 g | — |
| l(−) norephedrine | 2.0 g | 0.2 |
| Citric Acid, anhydrous | 1.2 g | 0.12 |
| Sodium Benzoate | 1.2 g | 0.12 |
| Sodium Chloride | 5.3 g | 0.53 |
| Sodium Saccharin | 2.5 g | 0.25 |
| Sucrose | 120.0 g | 12.0 |
| Sorbitol Solution | 450.0 g | 45.0 |
| Glycerin | 60.0 g | 6.0 |
| Mixed Fruit Flavor | 8.0 g | 0.8 |

-continued

| Ingredient | Per Liter | Percent (wt./volume) |
|---|---|---|
| (Natural & Artificial) FD & C yellow No. 6 | 0.1 g | 0.01 |
| Purified Water quantum sufficient(Q.S.) to one liter | — | — |

The purified water is warmed and the l(−)-norephedrine, citric acid anhydrous, sodium benzoate, sodium chloride, sodium saccharin, sucrose, and FD&C yellow No. 6 are dissolved. The solution is cooled and the sorbitol solution, glycerin, mixed fruit flavor and a sufficient quantity of purified water are added to make one liter of the immediate release liquid composition.

One teaspoonful (5 cc) contains 10 mg of l(−) norephedrine.

EXAMPLE X

An immediate release dosage composition, for use according to the present invention, is made comprising the following components:

| Ingredient | Per Tablet | Percent by Weight |
|---|---|---|
| (racemic mixture of d(+)-norephedrine and l(−)norephedrine)HCl | 37.5 mg | 9.9 |
| Microcrystalline cellulose | 100.0 mg | 26.5 |
| Compressible sugar | 200.0 mg | 53.0 |
| Sodium starch glycolate | 10.0 mg | 2.6 |
| Stearic acid | 15.0 mg | 4.0 |
| Talc | 15.0 mg | 4.0 |
| | 377.5 mg | |

All the ingredients are sized, dry blended and compressed into tablets on a tablet press.

EXAMPLE XI

A long acting release dosage composition, for use according to the present invention, is made comprising the following ingredients:

| Ingredient | Per Tablet | Percent by Weight |
|---|---|---|
| Guaifenesin | 400 mg | 51.3 |
| (racemic mixture of d(+)-norephedrine and l(−)-norephedrine)HCl | 75 mg | 9.6 |
| Carbomer | 117 mg | 15.0 |
| FD & C Blue #1 Aluminum Lake Dye | 3 mg | 0.4 |
| Compressible Sugar | 139 mg | 17.8 |
| Stearic Acid | 40 mg | 5.1 |
| Zinc Stearate | 6 mg | 0.8 |

-continued

| Ingredient | Per Tablet | Percent by Weight |
|---|---|---|
| | 780 mg | |

The guaifenesin, (racemic mixture of d(+)-norephedrine and l(−)-norephedrine) HCl, carbomer, dye and stearic acid are roller compacted and sized. The compressible sugar and zinc stearate are added and then compressed into tablets on a tablet press.

EXAMPLE XVII

A forty-four-year-old man suffering from nasal and sinus congestion and retention of thickened mucus and other respiratory secretions is orally given a tablet of 75 mg of a composition containing l(−)-norephedrine and guaifenesin twice a day. Administration of the above tablet results in nasal and sinus decongestion and drainage of the retained mucus and other respiratory secretions.

EXAMPLE XVIII

A three-year-old child afflicted with otitis media that is characterized by eustachian tube congestion and retention of thickened respiratory secretions, especially thickened mucus, is given a half teaspoon of the formulation of Example IX four times a day. Administration of the above liquid results in the drainage of the mucus and other respiratory secretions.

What is claimed is:

1. A method of inducing mucous secretion in the upper airways of a human afflicted with sinusitis or otitis media characterized by retention of thickened respiratory secretions, comprising orally administering to said subject a composition consisting of a safe and effective amount of l(−)-norephedrine, sufficient to induce mucous secretion in the upper airways.

2. A method according to claim 1 wherein said human is afflicted with sinusitis.

3. A method according to claim 1 wherein said human is afflicted with otitis media.

4. A method of inducing both nasal decongestion and mucous secretion in the upper airways of a human afflicted with sinusitis or otitis media characterized by both upper respiratory congestion and retention of thickened respiratory secretions, comprising orally administering to said subject a composition consisting of a safe and effective amount of l(−)-norephedrine, sufficient to induce both nasal decongestion and mucous secretion in the upper airways.

5. An oral composition for inducing upper respiratory mucous secretion consisting of a safe and effective amount of l(−)-norephedrine sufficient to induce mucous secretion in the upper airways of a human afflicted with sinusitis or otitis media and a pharmaceutically-acceptable excipient base.

* * * * *